(12) United States Patent
Moeller (10) Patent No.: US 12,121,707 B2
(45) Date of Patent: Oct. 22, 2024

(54) INJECTION DEVICE

(71) Applicant: Shaily Engineering Plastics Ltd., Gujarat (IN)

(72) Inventor: Claus Schmidt Moeller, Fredensborg (DK)

(73) Assignee: SHAILY ENGINEERING PLASTICS LIMITED, Gujarat (IN)

( * ) Notice: Subject to any disclaimer, the term of this patent is extended or adjusted under 35 U.S.C. 154(b) by 888 days.

(21) Appl. No.: 17/273,875

(22) PCT Filed: Sep. 2, 2019

(86) PCT No.: PCT/DK2019/000277
§ 371 (c)(1),
(2) Date: Mar. 5, 2021

(87) PCT Pub. No.: WO2020/048570
PCT Pub. Date: Mar. 12, 2020

(65) Prior Publication Data
US 2021/0330890 A1    Oct. 28, 2021

(30) Foreign Application Priority Data

Sep. 8, 2018   (DK) .......................... PA 2018 00555

(51) Int. Cl.
*A61M 5/315*   (2006.01)
*A61M 5/31*   (2006.01)

(52) U.S. Cl.
CPC .... *A61M 5/31551* (2013.01); *A61M 5/31501* (2013.01); *A61M 5/31585* (2013.01);
(Continued)

(58) Field of Classification Search
CPC ............ A61M 5/31528; A61M 5/3155; A61M 5/31551; A61M 5/31553; A61M 5/31585
See application file for complete search history.

(56) References Cited

U.S. PATENT DOCUMENTS 6,221,053 B1 *   4/2001   Walters ............. A61M 5/31551
                                                               604/211
2004/0267207 A1 *   12/2004   Veasey .............. A61M 5/31551
                                                               604/208
(Continued)

FOREIGN PATENT DOCUMENTS

EP     1 003 581 B1    5/2000
EP     2 201 972 A1    6/2010
(Continued)

OTHER PUBLICATIONS

International Search Report (Form PCT/ISA/210) for International Patent Application No. PCT/DK2019/000277, issued from the European Patent Office, date of mailing Dec. 4, 2019, 3 pages.

*Primary Examiner* — Kami A Bosworth
(74) *Attorney, Agent, or Firm* — Kilyk & Bowersox, P.L.L.C.

(57) ABSTRACT

An injection device is disclosed wherein a dose can be set by rotating a dose setting member, whereby a push button is elevated from one end of the device a distance proportional to the set dose from a position fixed relative to the housing, and wherein the set dose can then be injected by pressing the push button back to its non-elevated position, through which motion a screw will move approximately the same distance or a smaller distance. The invention provides a method of reducing the dose force and/or the push-button movement during injection.

6 Claims, 13 Drawing Sheets

(52) U.S. Cl.
CPC . *A61M 2005/3126* (2013.01); *A61M 5/31558* (2013.01); *A61M 2205/581* (2013.01); *A61M 2205/585* (2013.01)

(56) References Cited

U.S. PATENT DOCUMENTS

| | | | | |
|---|---|---|---|---|
| 2005/0261634 | A1* | 11/2005 | Karlsson | A61M 5/20 604/197 |
| 2006/0206057 | A1* | 9/2006 | DeRuntz | A61M 5/31551 604/224 |
| 2006/0258988 | A1* | 11/2006 | Keitel | A61M 5/31551 604/181 |
| 2012/0046643 | A1* | 2/2012 | Plumptre | A61M 5/31551 604/207 |

FOREIGN PATENT DOCUMENTS

| | | |
|---|---|---|
| JP | 2016518230 A | 6/2016 |
| WO | 01/95959 A1 | 12/2001 |
| WO | 2011/060785 A1 | 5/2011 |
| WO | 2012/037938 A1 | 3/2012 |
| WO | 2014/187811 A1 | 11/2014 |

* cited by examiner

INJECTION DEVICE

FIELD OF INVENTION

The invention relates to a dose delivery device, wherein a dose can be set by rotating a dose setting member, whereby a push button is elevated from one end of the device, and wherein the set dose can be injected by pressing the push button back to its non-elevated position, thereby axially moving a screw co-operating with the plunger in a cartridge and expelling a medicament out of the cartridge through a needle.

DESCRIPTION OF THE RELATED ART

EP 0 327 910 describes a device in which a dose is set by rotating a tubular injection button engaging a threaded screw, thereby causing the injection button to elevate from the end of the injection device. By pressing down the injection button until abutment with a fixed stop the threaded screw is moved a distance corresponding to the movement of the injection button. The screw abuts a plunger in a cartridge and medicine is expelled from the cartridge. This kind of injection device transmits the injection force directly to the plunger of the cartridge but provides no gearing, i.e. the linear movement of the injection button corresponds exactly to the linear movement of the screw.

However, the above described device does not provide a numbered dose dial, and the amount of a set dose must be calculated by adding a one-digit scale with a ten-digit scale. As all parts of the dose setting mechanism conducts only linear movements when a set dose is injected the incremental size of a unit in the dose setting mechanism is very small, and a dose can only be set to and displayed as every second unit.

EP 1 003 581 describes a number of methods to achieve a dose setting providing a gearing between the axial movement of the screw and axial movement of the dose setting member and/or push-button, so that a dose dial with sufficient space for numbers to be added. In one embodiment a dose setting member with printed numbers on the cylindrical surface is engaging a thread in the housing with a higher lead than the lead on a screw. When pressure is added to an injection button the screw is rotationally coupled to the dose setting member and as the screw is rotated in a threaded nut fixed in the housing it is moved forward until the dose setting member abuts a rotational stop.

This device, however, is complicated and contains many layers to provide all the functionality, and this has the consequence that the thread engagement between the dose dial and the housing becomes rather big, and thereby the injection force will be relatively high and the movement of the push-button during injection will be relatively long.

WO 2011/060785 describes a device with a numbered dose dial and with no gearing. A screw is engaged with the housing via a not self-locking thread connection. A ratchet is rotationally coupled to the screw and preventing the screw from rotating backward thereby moving back into the device. A nut which is engaged with the thread of the screw is rotationally locked to a dose setting member during dose setting. The nut also comprises the numbers indicating the amount of a set dose. During the injection sequence the nut is initially released from the dose setting member, then rotationally coupled to the ratchet and the screw and thereafter a continued pressure on the push-button causes the screw, the ratchet and the nut to rotate and to move forward due to the not self-locking thread connection between the screw and the housing.

A disadvantage of this device is that the numbered dose dial are moves during the initial movement of the push-button, which makes it difficult to read the numbers during injection.

It is an objective of the present invention to provide a non-complicated and small injection device comprising a numbered dose dial, and which provides a low injection force and a low push-button movement during injection, and which also provides an easy reading of the set dose and remaining dose during dose setting and injection.

BRIEF DESCRIPTION OF THE INVENTION

The invention relates to an injection device comprising:
a housing having a first thread,
a screw having a second thread and a non-circular cross section,
a driver having a third and a fourth thread having the same lead and headed in the same direction,
wherein:
the screw rotates during injection,
the third thread of the driver engages the first thread of the housing and the fourth thread of the driver engages the second thread of the screw,
during dose setting the driver rotates and moves axially while the screw does not rotate or move axially, and
during injection the screw and the driver rotate together.

In this way the dose force on the driver is transferred directly to the screw without first being transformed to rotational movement and then back to linear movement with a resulting loss of energy. There is no load on the rotational movement and thereby the energy loss due to the rotation is very low. Furthermore, it is possible to use the mechanism for both a device with and without a gearing.

In an embodiment of the invention a numbered dose dial displaying the amount of set dose is engaged with a fifth thread in the housing having a higher lead than the third and the fourth threads on the driver and the driver is engaging the dose dial via a track allowing axial movement. Hereby it is possible to select a suitable gearing ratio for the device to have the dose force reduced.

In a further embodiment of the invention during injection the screw and the driver are rotationally coupled by means of a connecting tube which is rotationally locked to the screw via the non-circular cross-section of the screw and which is capable of moving axially relative to the screw and which during injection is rotationally coupled to the dose dial. In this way the rotational movements of the screw and the driver can be synchronized by through the dose dial, even though the dose dial has a longer axial movement then the driver.

In a further embodiment of the invention the driver is coupled to a dose selector during dose setting and decoupled during injection and the driver and the dose selector travels the same distance during dose setting and injection. In this way a very simple device comprising only a few parts can be made and the movement of the push-button will be very low. This also gives the possibility of having the dose setting clicks arranged between the dose selector and the housing.

In an even further embodiment of the invention a clutch is provided between the dose dial and the connecting tube and the clutch couples the dose dial and the connecting tube together during injection. This allows that the push on the push-button can directly couple the connecting tube and the driver together.

In an even further embodiment of the invention a bidirectional ratchet is provided between the dose dial and the connecting tube and the bidirectional ratchet indexes the dose dial on specific rotational positions around the revolution. In this way it is ensured that the number reflecting the set dose is displayed precisely.

In a further embodiment of the invention a unidirectional ratchet is rotationally coupled to the screw but axially movable relative to the screw and the ratchet prevents the screw from moving toward the push-button end. This ensures that the screw will not rotate along with the connecting tube during dose setting.

The objectives of the invention can be obtained by an injection device comprising a threaded screw, which is engaging the internal thread of a driver. The driver also has an external thread of the same lead as the internal thread headed in the same direction and engaging a nut fixed in the housing. The driver is furthermore rotationally connected with a numbered dose dial, which is engaging the housing via a thread with a bigger lead than the threads on the driver and the dose dial. A unidirectional ratchet cooperating with teeth in the nut fixed in the housing is rotationally but not axially connected to the screw, and also a connecting tube is rotationally but not axially connected to the screw. Between the dose dial and the connecting tube, a bidirectional ratchet is arranged.

A dose selector is integrated with the dose dial. When a dose is set by rotating the dose selector the unidirectional ratchet will prevent the screw and the connecting tube from rotating and the bidirectional ratchet between the connecting tube and the dose dial will click and position the dose dial on equally spaced increments around the revolution. The driver is rotated along with the dose dial, but as the lead on the external thread engaging the nut fixed in the housing is smaller than the lead on the dose dial engaging the housing, the driver is caused to move up a smaller distance than the dose dial. As the internal and the external thread on the driver has the same lead the screw will not move up or down when a dose is set. If a set dose is corrected the torque arising from the unidirectional ratchet and the resistance in the cartridge, which together are bigger than the torque arising from the bidirectional ratchet between the connecting tube and the dose dial, prevents the screw from rotating.

When the set dose is injected a push-button, which is axially locked to the connecting tube, but capable of rotating, is pushed down. This pushes the connecting tube into rotational engagement with the dose dial and further push on the push-button causes the dose dial to rotate due to the thread engagement with the housing. Thereby also the connecting tube, the screw, the driver and the unidirectional ratchet will rotate, and the unidirectional ratchet will produce a clicking sound. As both the driver and the screw rotate the screw will move down with the same speed as the driver causing the medicament to be expelled.

To prevent that a dose higher than the remaining content of the cartridge is set the thread on the screw is provided with a stop in the end headed towards the push button. As described above the unidirectional ratchet prevents the screw from rotating during dose setting, and further dose setting will therefore be prevented when the internal thread on the driver abuts the stop on the screw thread.

In another embodiment there is no gearing between the movement of the push-button and the screw and it is the thread engagement between the nut fixed in the housing and the driver that rotates the injection mechanism during injection. A nut assembly comprises a dose dial with numbers and a driver fixed to each other and is engaging the screw in an internal thread and the housing in an external thread. The screw is rotationally locked to a connecting tube and to a unidirectional ratchet. A combined dose selector and push-button is rotationally coupled to the nut assembly during dose setting and they are maintained in engagement by means of a spring located between the connecting tube and the nut assembly. When a dose is set, the dose selector is rotated in increments defined by flexible protrusions on the dose selector cooperating with grooves in the housing. The nut assembly rotates along and this rotation elevates the nut assembly and the dose selector. When a set dose is injected the combined dose selector and push-button is pushed which disengaging it from the dose dial and instead engaging the connecting tube with the nut assembly. Due to the thread engagement between the driver, which is part of the nut assembly, and the thread in the housing further pushing will cause the nut assembly, the connecting tube, the screw and the unidirectional ratchet to rotate and the ratchet will produce a clicking sound.

A transparent window may be added to the housing to protect the user from touching the dose dial or a magnifier may be added to enlarge the number and make it more readable. A window or a magnifier can also act as a stop for the maximum settable dose by having an inwardly headed protrusion cooperating with the dose dial or with another part of the device.

In another embodiment the dose dial has an outer thread with a lead of e.g., the double of the lead of the screw. A window item which may also comprise a magnifier, and which is axially but not rotationally movable relative to the housing, is engaging the thread of the dose dial. When the dose dial rotates up along the screw, the window item moves down a bigger distance than the dose dial, and in that way more space on the dose dial is provided for numbers. A prolonged hole in the housing allows the window item to move up and down.

Alternatively, the outer thread on the dose dial has a very high lead and engages the internal thread of an enlarging dose dial provided with dose indicative numbers and engaged with an internal thread in the housing. If the lead between the enlarging dose dial and the housing is bigger than the lead between the dose dial and the housing, then more space for the numbers along the axis of the device is provided. If also the high lead thread between the dose dial and the enlarging dose dial is handed in a direction that makes the enlarging dose dial rotate faster than the dose dial, then more rotationally space for the numbers is provided as well. To ease assembly the rotational connection between the dose dial and the enlarging dose dial could be a straight key/groove connection instead of a thread connection, which then would only provide more axial space for the numbers.

The dose delivery device may be designed to be either disposable or reusable and to contain one, two or multiple cartridges at the time. If the dose delivery device is designed to be reusable, the screw must be capable of rotating backward when the cartridge holder is disconnected.

FIGURES

In the following the invention is described in further details with reference to the drawings, wherein.

DETAILED DESCRIPTION

In the following the terms "up" and "down", "upper" and "lower", "upward" and "downward" and "left" and "right" refer to the drawings and does not necessarily correspond to a situation of use. The term "axial" is to be construed as parallel with the main axis of the device.

Parts, which are fixed together, are marked with individual part numbers. However, they may also be marked as one part, and functionally features from a first part fixed to a second part are also to be considered as being features of the second part.

FIGS. 1-5 show a device according to the invention having a gearing, also called a mechanical advantage, between the push-button and the screw. On FIG. 1 the device is seen in an oblique view. Visible is the housing 1 with a window 11 where the amount of a set dose is displayed, and the dose selector 41 integrated with the dose dial 2 with printed numbers and by which a dose is set and reset by rotating the dose selector clockwise and anticlockwise. The cartridge holder 10 comprises a thread 31 for the attachment of a double-ended needle. The cartridge holder 10 also contains the medicament filled cartridge (not visible). The medicament filled cartridge comprises a plunger, which, via a foot 9 (visible on FIG. 3), cooperates with a screw 7 to expel a set dose of medicament from the cartridge and out through the needle when the push-button 4 is pushed by a user. The cooperation between the different elements of the device will be described in the following.

It should be understood that the dose selector 41, 134, 234, 334 of the shown embodiments is an element by which a dose can be both set and reset and, in some embodiments, also pushed to inject the set dose. The dose selector can be an individual element, or it can be integrated with the dose dial or other parts. In embodiments where the dose selector is only for setting and resetting the dose a separate push-button 4, 355 for injecting the set dose is provided.

The dose setting and the dose injection mechanisms are highly integrated and the change from dose setting mode to dose injection mode is caused by an initial movement of a push-button 4, 355 or a dose selector 134, 234 before the actual injection starts.

Figure 1:
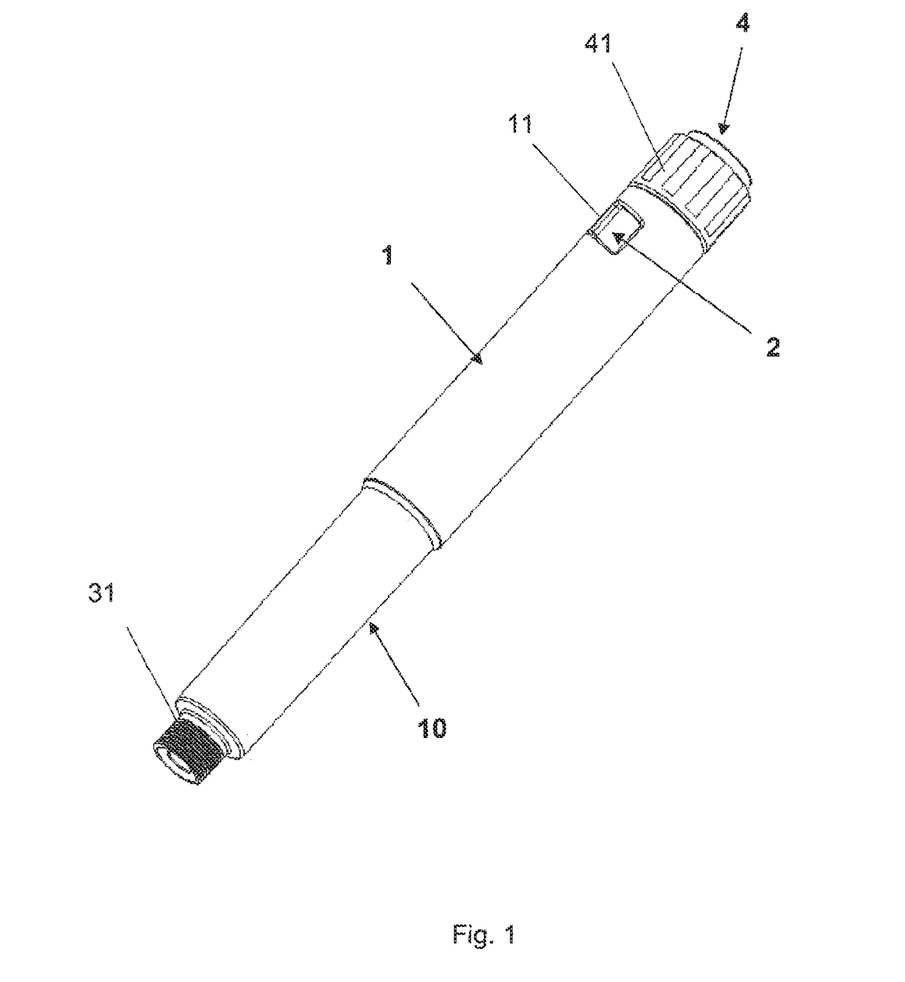
FIG. 1 shows a perspective view of a device according to the invention.
Figure 2:
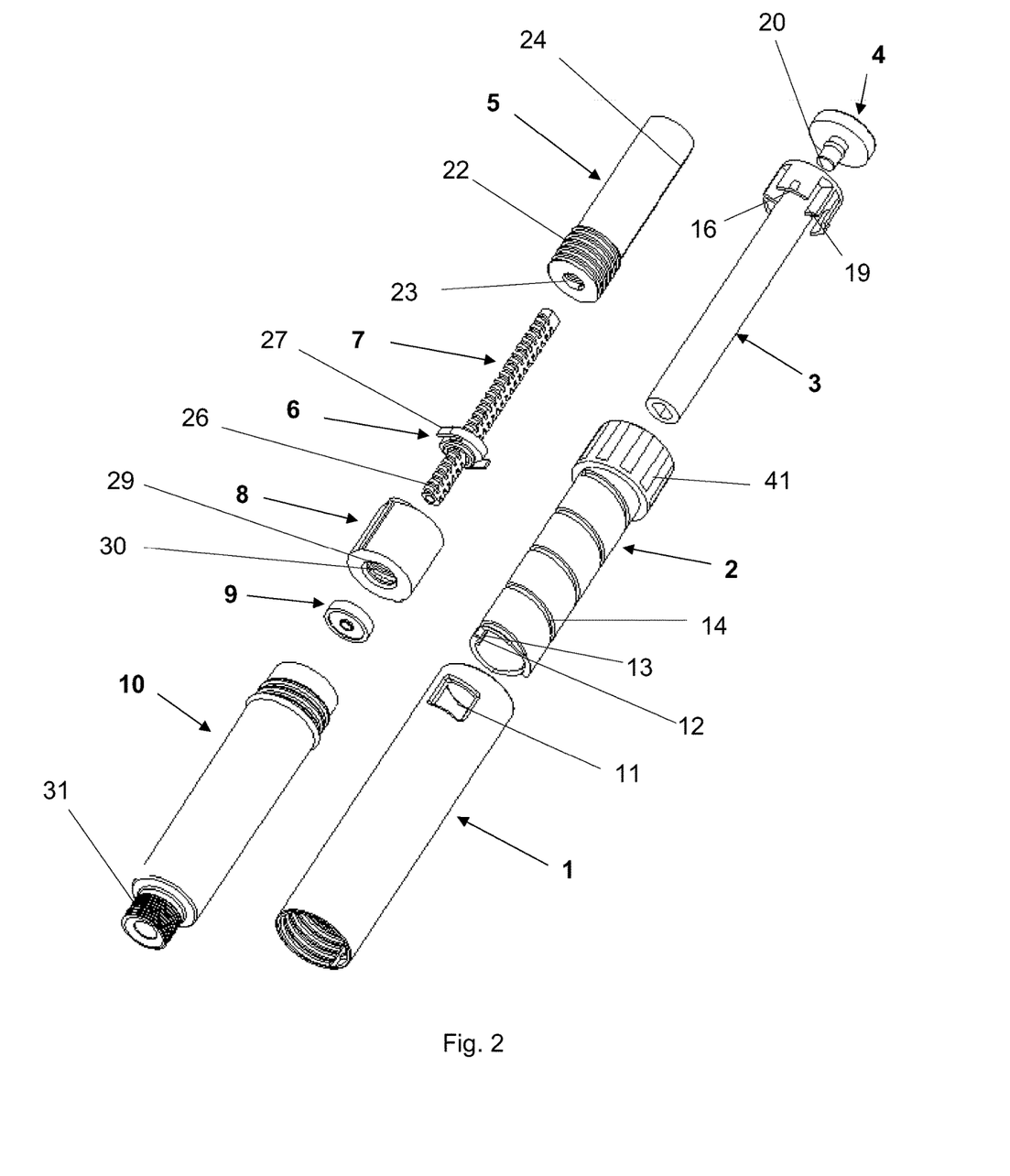
FIG. 2 shows an exploded view of a device according to the invention with a gearing, FIG. 3 schematically shows a vertical sectional view of a device according to the invention with a gearing and ready to set a dose, FIG. 4 schematically shows a vertical sectional view of a device according to the invention with a gearing and where a dose has been set, FIG. 5 schematically shows a vertical sectional view of a device according to the invention with a gearing and where the push-button has been pushed and the medicament has been injected.
Figure 3:
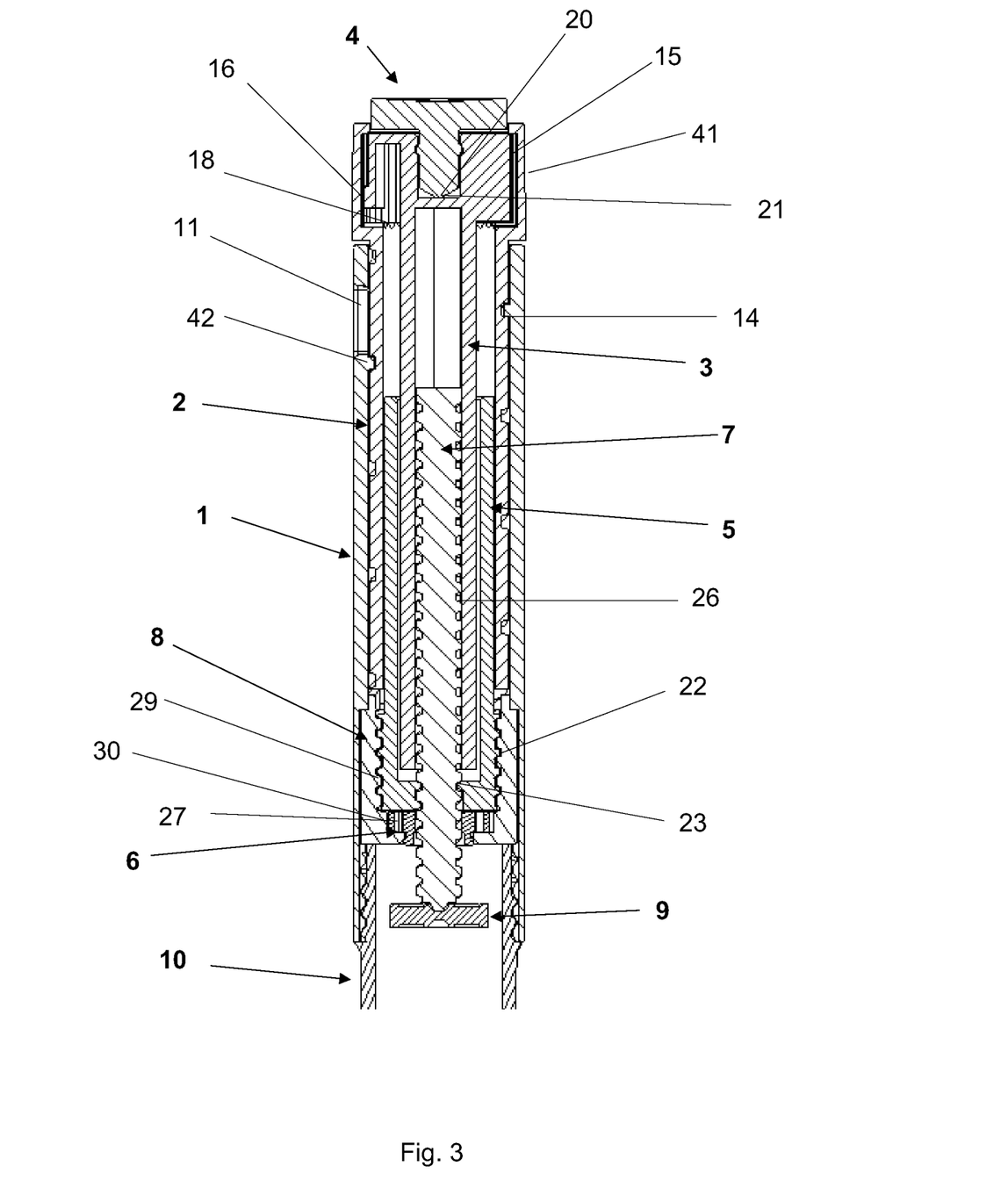

As shown in FIG. 3 a screw 7 having a thread 26 is engaging the internal thread 23 of a driver 5. The driver 5 also comprises an external thread 22, which engages the thread 29 of a nut 8 fixed in the housing 1, and which has the same lead as the thread 26 of the screw 7. The screw 7 has a non-circular cross section. A unidirectional ratchet 6 with one or more ratchet arms 27, which cooperates with teeth 30 inside the nut 8, rotates together with the screw 7 but is axially fixed in the housing 1. The connecting tube 3 also rotates together with the screw 7 and is capable of sliding axially relative to the screw 7. A dose dial 2 with a thread 14 engaged with the thread 42 in the housing 1, and which is integrated with a dose selector 41, is rotationally coupled to the driver 5 via an axial key/groove connection 13/24 (see FIG. 2). A push button 4 is axially locked to the connecting tube 3 but is free to rotate.

The connecting tube 3 has three ratchet arms (best seen on FIG. 2) with protrusions 16 cooperating with grooves 15 inside the dose selector 41 (integrated with the dose dial 2) to form a bidirectional ratchet. The torque induced by this ratchet must be smaller than the torque induced by the unidirectional ratchet 6. This will be further explained.

When a dose is set the dose selector 41 with the integrated dose dial 2 is rotated. Due to the thread engagement 14/42 between the dose dial 2 and the housing 1 the dose selector 41 and the dose dial 2 elevates out of the housing 1 a distance equivalent to the set dose. The driver 5 rotates along with the dose dial 2 due to the key/groove connection 13/24, but due to the thread engagement 22/29 between the driver 5 and the nut 8 fixed in the housing, and because this thread has a lower lead, the driver 5 elevates less than the dose dial 2.

The screw 7 is prevented from rotating during dose setting by the unidirectional ratchet 6 as the direction of rotation is in the locking direction. As the lead of the internal thread 23 and the external thread 22 on the driver 5 are the same the screw 7 does not move up or down during dose setting. The connecting tube 3 does not rotate either due to the rotational connection with the screw 7, and v-shaped grooves 18 in the bottom of the dose selector 41 (see FIG. 3) cooperate with v-shaped teeth 19 on the connecting tube 3 (see FIG. 2) in forcing the connecting tube 3 out of engagement with the dose selector 41 when the dose selector is rotated. The protrusions 16 on the click arms on the connecting tube 3 produces a clicking sound and index the dose selector 41 around the revolution due to the cooperation with the grooves 15 inside the dose selector 41.

When the set dose is injected the push-button 4 is pushed. This will first of all lock the connecting tube 3 rotationally to the integrated dose selector 41 and dose dial 2 as the v-shaped teeth 19 on the connecting tube 3 engage with the v-shaped grooves 18 inside the dose selector 41. Now a continued press on the push-button 4 causes the dose dial 2 to rotate due to the not self-locking thread engagement 14/42 between the dose dial 2 and the housing 1. The connecting tube 3, the screw 7, the driver 5 and the unidirectional ratchet 6 are all rotationally locked to the dose dial 2 during injection and will rotate as well. As the screw 7 during injection is prevented from rotating relative to the driver 5 and as it is prevented from moving up and down relative to the driver 5 due to thread engagement 23/26 with the driver 5, the screw will move the same distance as the driver, and the medicament contained in the cartridge will be expelled. The injection stops when the stopping surfaces 12 (see FIG. 2) abut corresponding surfaces on the nut 8 fixed in the housing.

To minimize the loss of energy in the system, sliding surfaces 20/21 with a small contact diameter are provided between the push-button 4 and the connecting tube 3.

To prevent that a dose larger than the remaining content of the cartridge can be set, the thread 26 on the screw 7 is provided with a stop in the end pointing towards the push-button 4. As the screw 7 is prevented from rotating in the dose set direction by the unidirectional ratchet 6 further rotation of the dose selector 41 is prevented when the internal thread 23 on the driver 5 abuts the thread stop.

In the following the operations of setting and injecting a dose on the above described device will be described.

On the device showed on FIG. 3 a dose has not yet been set. The dose dial 2 integrated with the dose selector 41, the connecting tube 3 and the driver 5 are in their non-elevated zero position.

Figure 4:
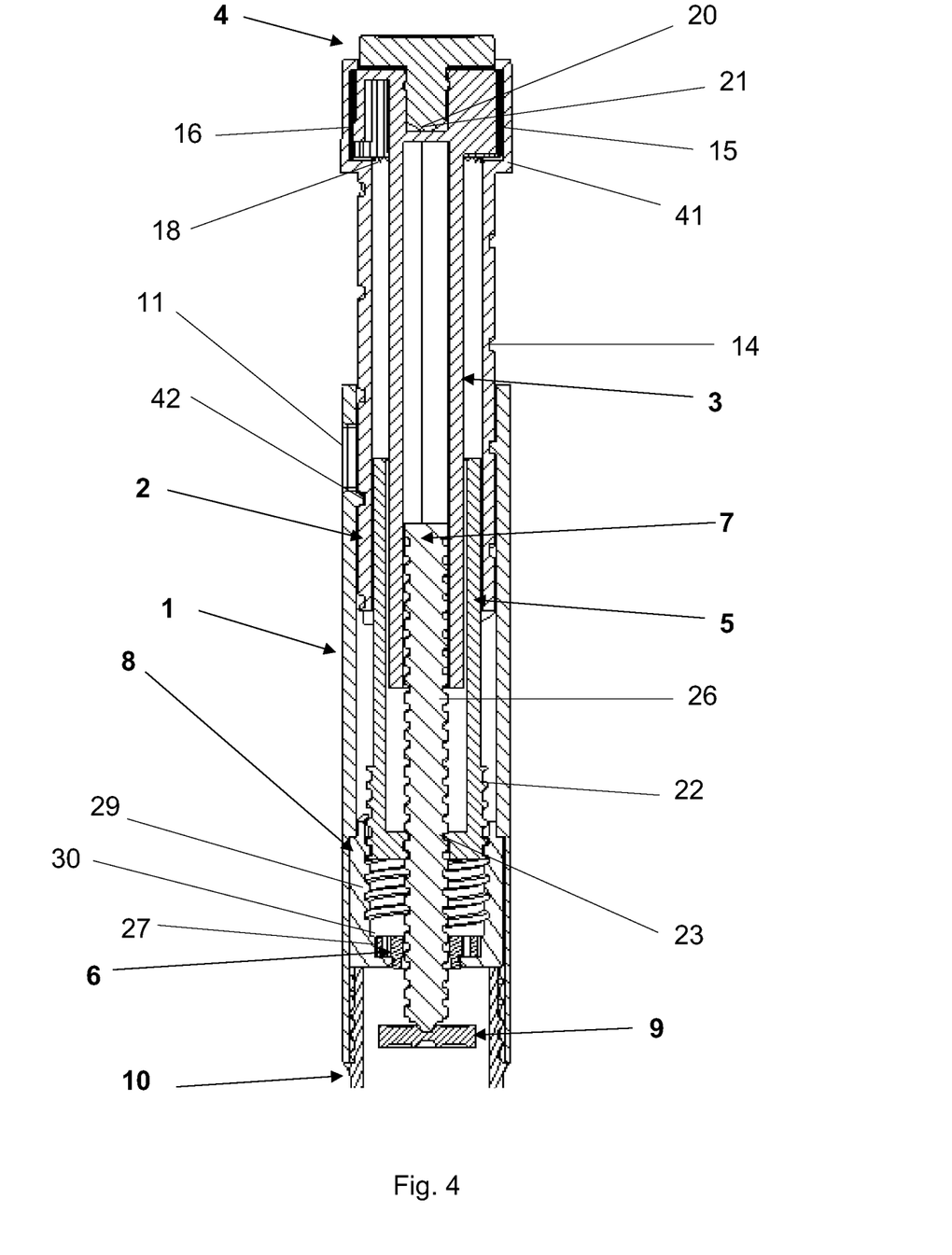

On FIG. 4 a dose is set and it can clearly be seen that the dose dial 2 integrated with the dose selector 41 has elevated a distance. The driver 5 has elevated a distance but it is also clear that the distance elevated by the driver 5 is smaller than the distance elevated by the dose dial 2. The connecting tube 3 has moved axially together with the dose selector 41 but it has not rotated due to the rotational connection with the screw 7, which is prevented from rotating by the unidirectional ratchet 6.

Figure 5:
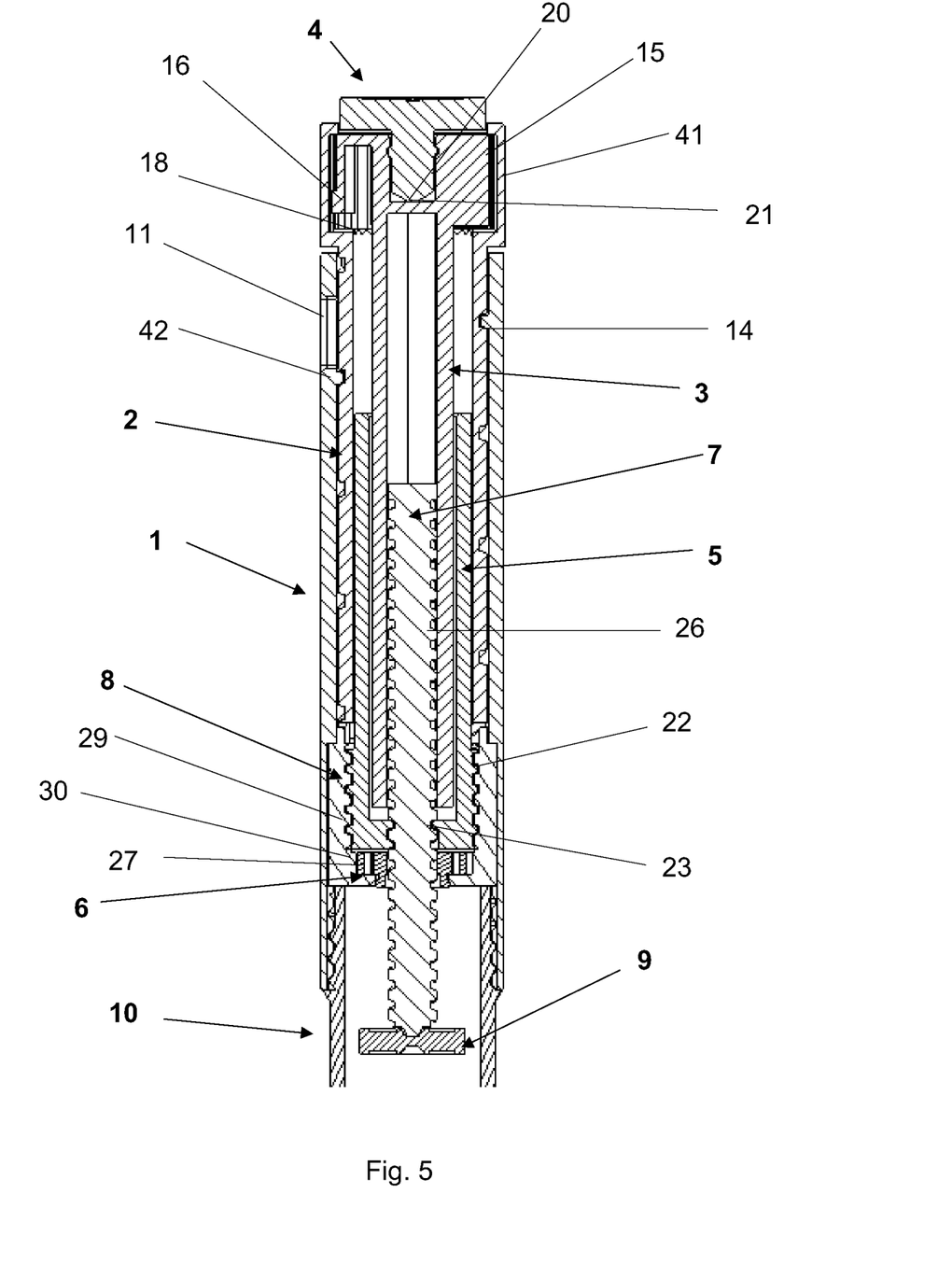

On FIG. 5 the set dose has been injected and the only difference from FIG. 3 is that the screw 7 has moved a distance and that the unidirectional ratchet 6 has been rotated an angle together with the screw 7.

FIGS. 6-11 show an embodiment according to the invention without a gearing. In this embodiment the push-button is integrated with the dose selector 134 and moves the same distance as the screw 107 during dose setting and injection.

Figure 6:
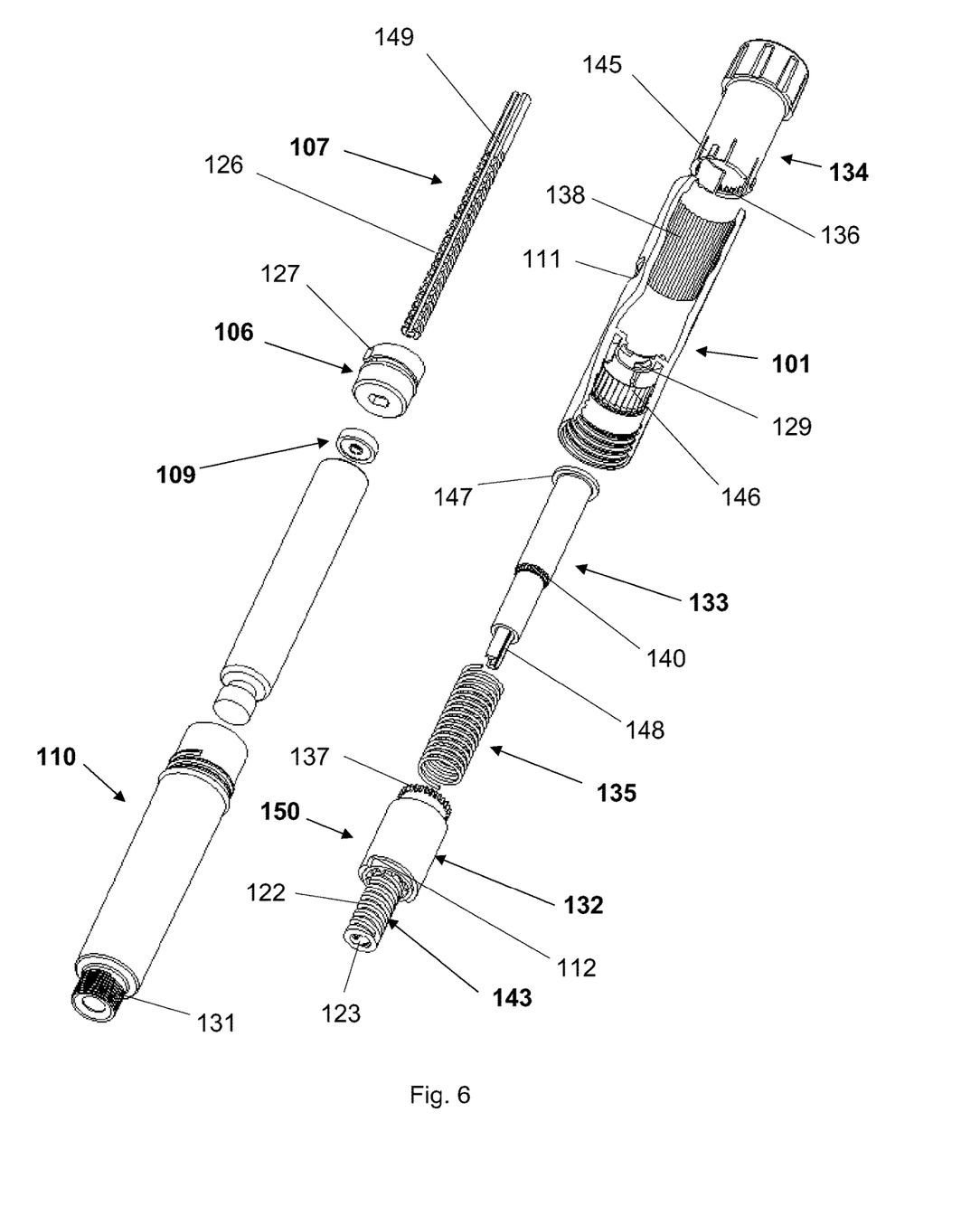
FIG. 6 shows an exploded view of a device according to the invention without a gearing.
Figure 7:
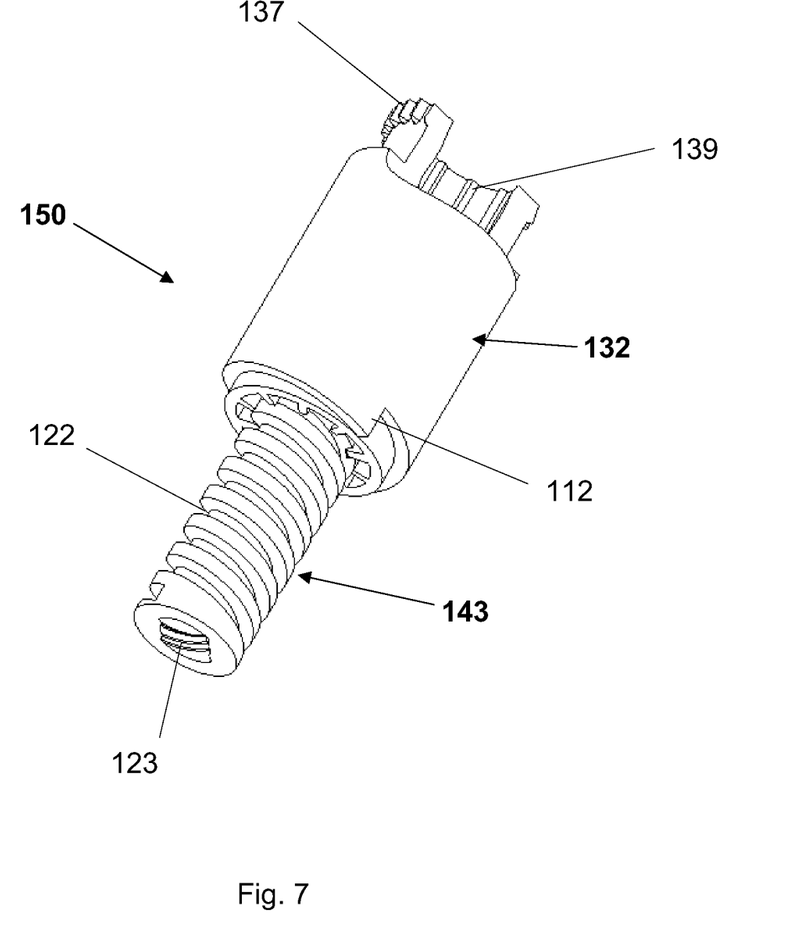
FIG. 7 shows a perspective view of a nut assembly for a device according to the invention without a gearing, FIG. 8 schematically shows a vertical sectional view of a device according to the invention without a gearing and ready to set a dose, FIG. 9 schematically shows a vertical sectional view of a device according to the invention without a gearing and where a dose has been set, FIG. 10 schematically shows a vertical sectional view of a device according to the invention without a gearing and where the push-button has been pushed the initial distance before the injection starts, FIG. 11 schematically shows a vertical sectional view of a device according to the invention without a gearing where the push-button has been pushed and the medicament has been injected, FIG. 12 schematically shows a vertical sectional view of a device according to the invention without a gearing and with an additional enlarging dose dial with big numbers.

On FIG. 6 the different parts and features of the device can be seen. As seen on FIG. 7 a driver 150 comprises a threaded part 143 and a dose dial 132 fixed together. The driver 150 is engaging the screw 107 in a thread connection 123/126. The driver 150 is also engaging the housing 101 in a thread connection 122/129 having the same lead and headed in the same direction as the thread connection 123/126 between the threaded part 143 and the screw 107. The dose dial 132 has a cylindrical portion with numbers indicative of the size of a set dose. The dose selector 134 is rotationally coupled to the driver 150 during dose setting via teeth 136 on the dose selector 134 engaged with teeth 137 on the dose dial 132. A connecting tube 133 is rotationally locked to the screw 107 via tracks 148 protruding along the entire length of the connecting tube 133 and engaging grooves 149 on the screw 107. A spring 135 is placed between a flange 147 on the connecting tube 133 and the dose dial 132. The connecting tube 133 axially engages the dose selector 134 in a gliding bearing 120/121 and the spring 135 ensures that the dose selector 134 and the dose dial 132 are engaged when the dose selector 134 has not been pushed yet.

When a dose is set the dose selector 134 is rotated and click protrusions 145 on the outside of the dose selector 134 produce a clicking sound and index the dose selector 134 around the circumference in cooperation with grooves 138 on the inner periphery of the housing 101. This will also rotate the driver 150 and the driver will display the amount of the set dose in a window 111 in the housing 101. The screw 107 is rotationally locked to a unidirectional ratchet 106 with ratchet arms 127 cooperating with teeth 146 inside the housing 101. The screw 107 is prevented from rotating during dose setting as this is the locking direction of the ratchet 106, and during dose correction because of the torque arising from the ratchet 106 and the resistance in the cartridge. The ratchet 106 cannot move axially relative to the housing 101.

To inject the set dose the dose selector 134 is pressed down. This disconnects the dose selector 134 from the dose dial 132 and presses down the connecting tube 133. This will then rotationally connect the connector 133 with the dose dial 132 due to teeth 140 on the connector 133 and teeth 139 (see FIG. 7) inside the dose dial 132. Now the driver 150, the connecting tube 133 and the screw 107 are rotationally locked together and a further push on the dose selector 134 causes the three elements to rotate and move forward due to the thread engagement 122/129 between the driver 143 and the housing 101, causing the medicament in the cartridge to be expelled.

In the following the operations of setting and injecting a dose on the above described device without a gearing will be described.

Figure 8:
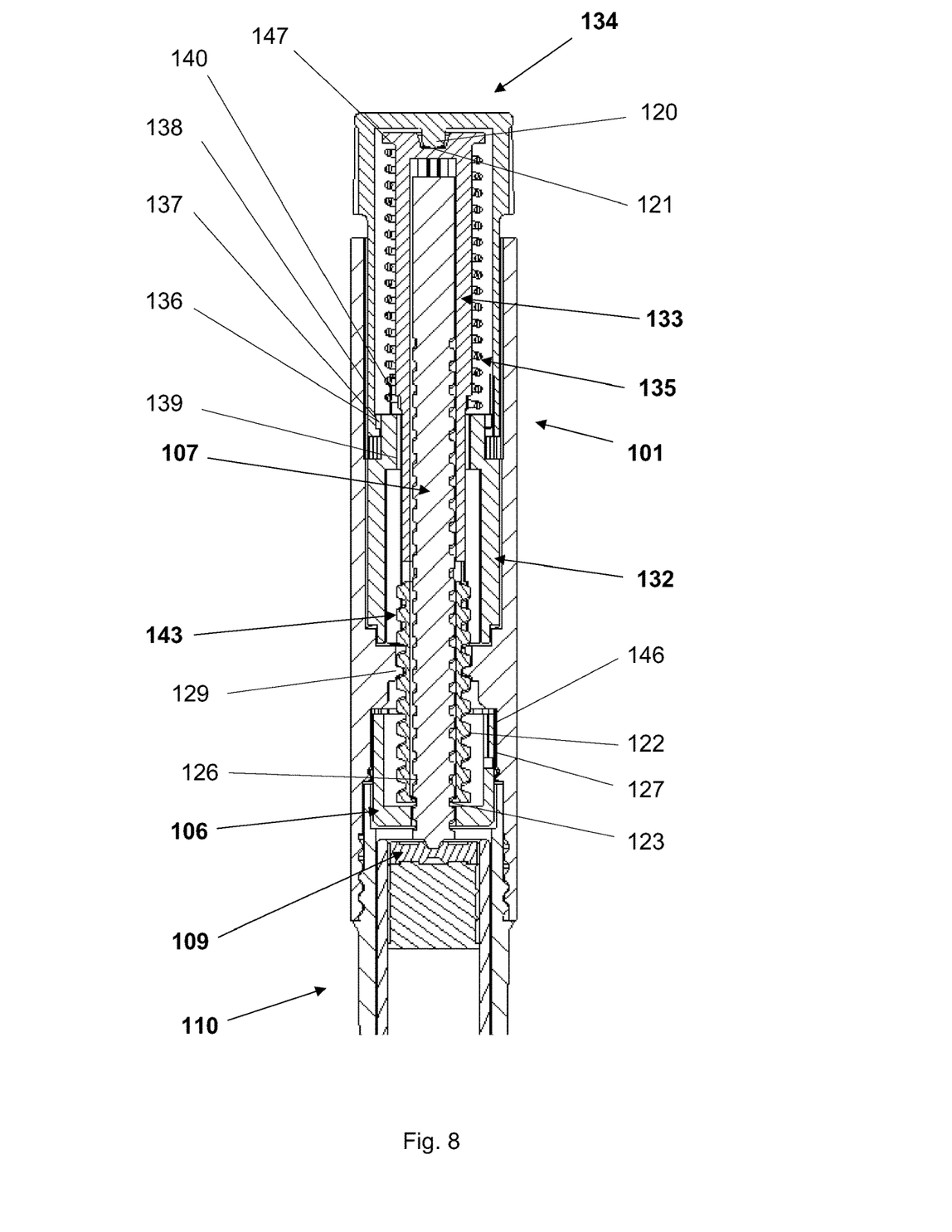

FIG. 8 shows a device where a dose has not yet been set. The dose selector 134 is engaging the dose dial 132 because of the spring 135 acting on the connector 133 and the dose selector 134. The dose selector 134, the driver 150 and the connector 133 are in the zero position, and the screw 107 is in the initial position.

Figure 9:
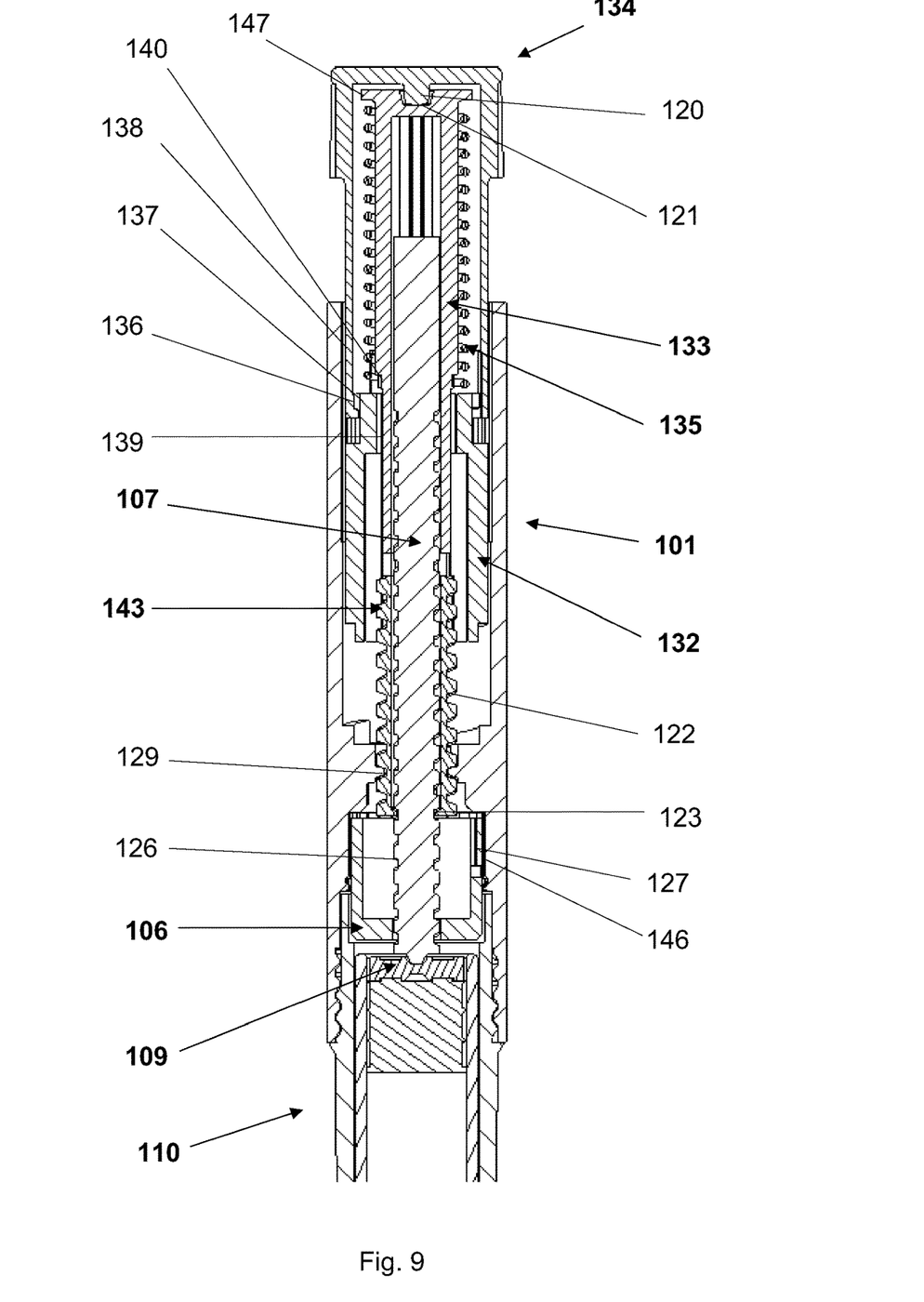

In FIG. 9 a dose has been set. The dose selector 134 and the driver 150 has been rotated an angle, and because of the thread connection 122/129 between the threaded part 143 and the housing 101 the dose selector 134 and the driver 150 have elevated a distance. The connector 133 has moved up in the housing 101 as well due to the spring 135, which ensures that the connector 133 always follow the axial movements of the dose selector 134, but it has not been rotated. The screw 107 has not moved.

Figure 10:
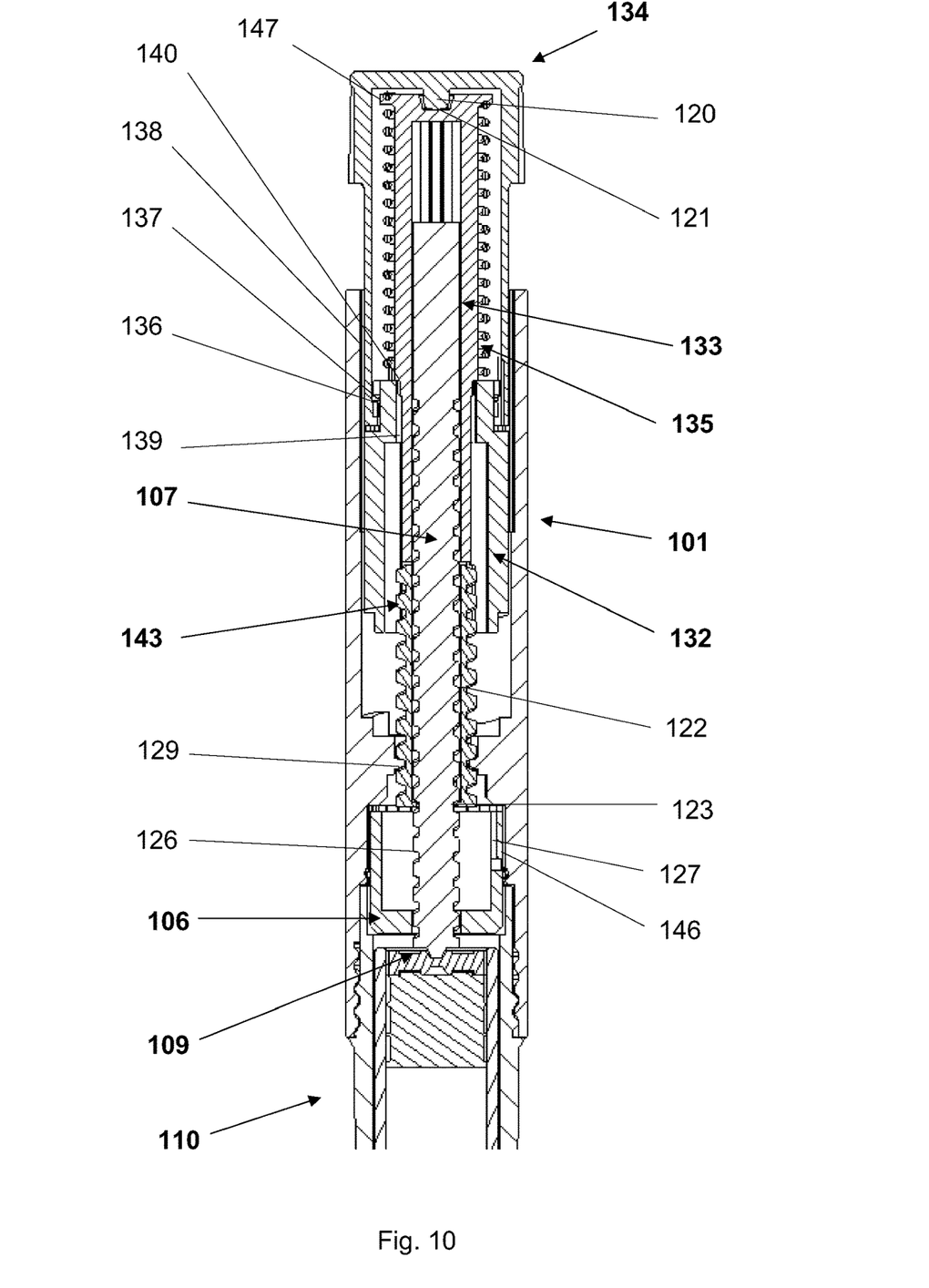

In FIG. 10 the dose selector 134 has been pushed the initial distance. This has caused the dose selector 134 and the dose dial 132 to disconnect and the connector 133 and the dose dial 134 to connect, and thereby the driver 150, the connector 133, the screw 107 and the ratchet 106 are rotationally connected. The dose selector 134, however, is set free to rotate relative to the connected parts. The screw 107 has not yet moved.

Figure 11:
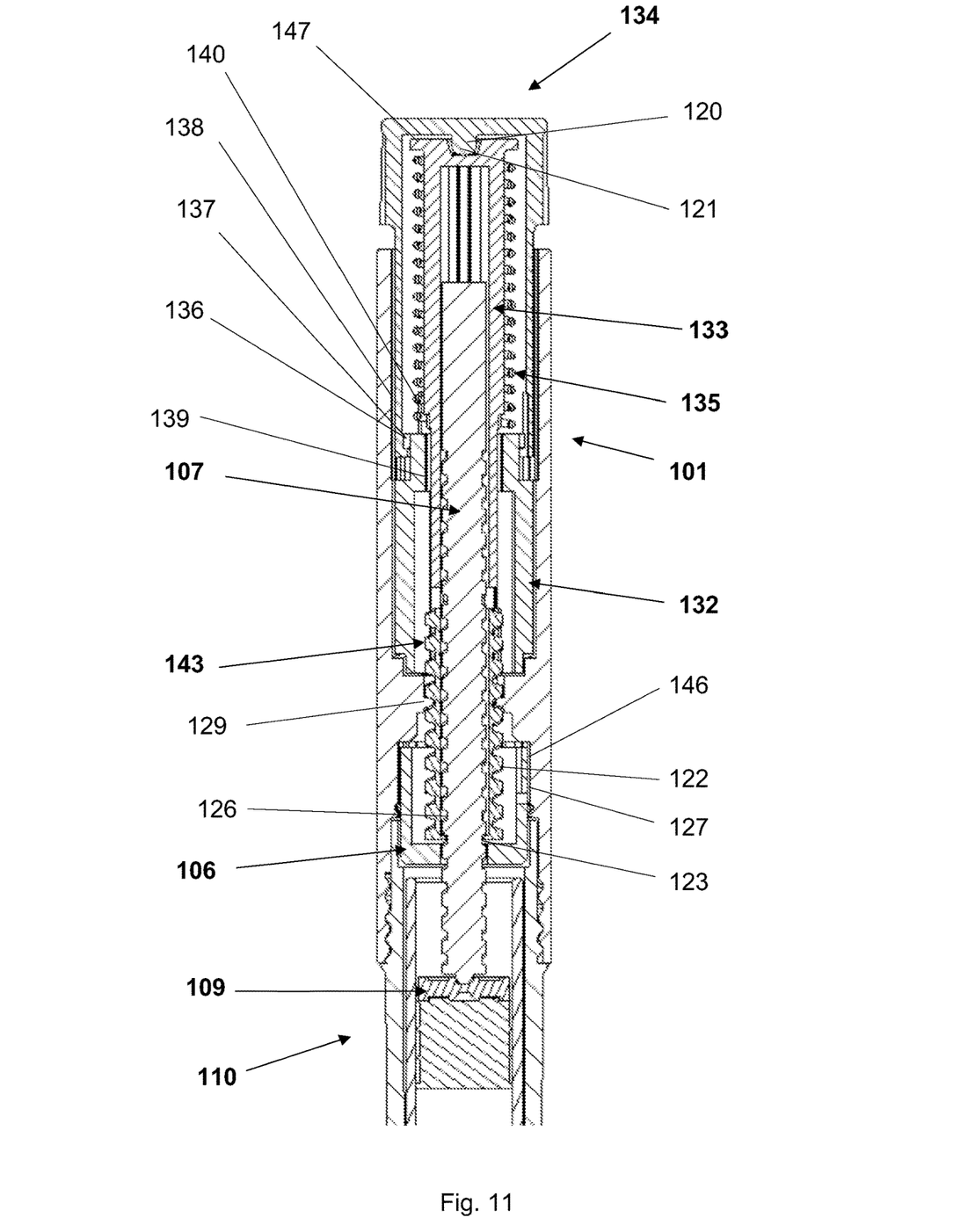

In FIG. 11 the injection has been fulfilled. The rotationally coupled parts (driver 150, connector 133, screw 107 and ratchet 106) have been rotated down to the initial zero position defined by the stop surfaces 112 on the dose dial 132 (see FIG. 7) and corresponding surfaces inside the housing 101. The rotational movement of the parts is caused by the not self-locking thread engagement 122/129 between the threaded part 143 and the housing 101. The dose selector 134 has also been pushed down but without rotating and the axial force has been transmitted to the connector 133 via the glide bearing connection 120/121. The screw 107 has moved the same distance as the dose selector 134.

Figure 12:
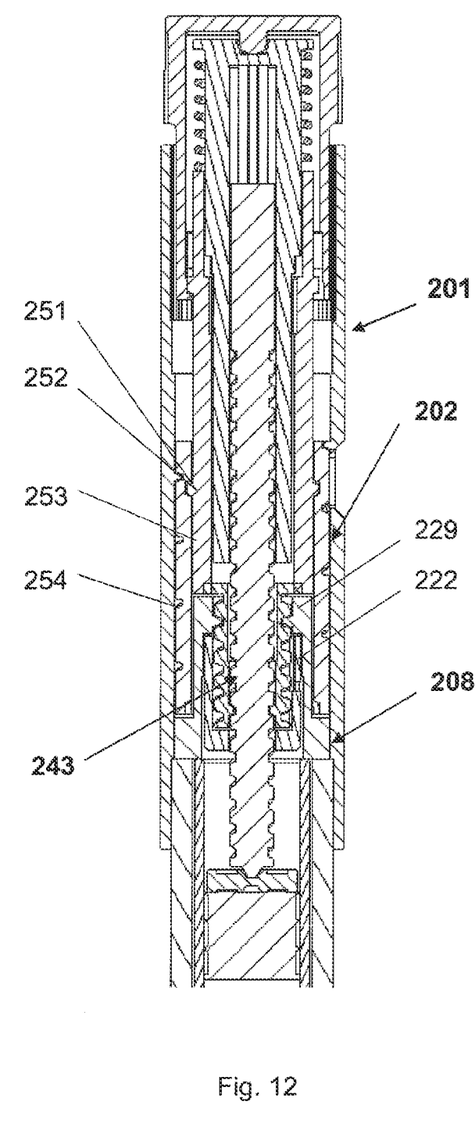
Figure 13:
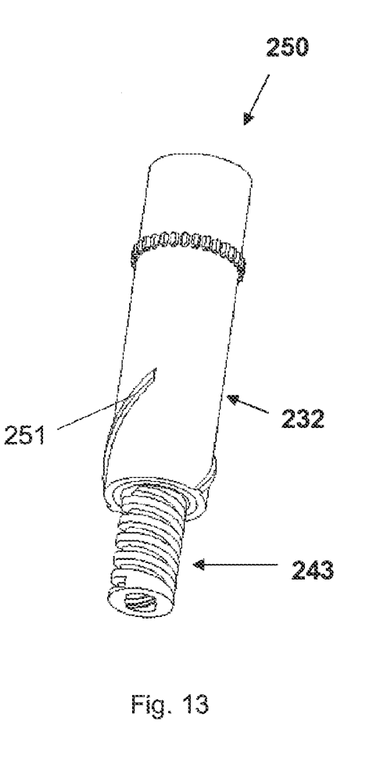
FIG. 13 shows a perspective view of a driver assembly comprising an enlarging dose dial fixed together with a threaded part, FIG. 14 schematically shows a vertical sectional view of a device according to the invention without a gearing and with low internal resistance.

FIGS. 12 and 13 show a non-geared device similar to the embodiment shown in FIGS. 6-11 but further comprising an enlarging dose dial 202. Parts and features not referred to corresponds to parts and features of the embodiment described in FIGS. 6-11. On this embodiment the numbers indicative of the dose size are printed on the enlarging dose dial 202 rather than on the dose dial 232 fixed together with the threaded part 243 (the dose dial 232 and the threaded part 243 together forming the driver 250 as shown in FIG. 13). A helical track 251 with a high lead on the dose dial 232 is engaging an internal track 252 inside the enlarging dose dial 202 and the enlarging dose dial 202 further has an external thread 253, which is engaging an internal thread 254 in the housing 201. The lead direction of the track connection 251/252 between the dose dial 232 and the enlarging dose dial 202 is so arranged that the enlarging dose dial 202 rotate more than the dose dial 232 when a dose is set and injected. As the thread connection 253/254 between the enlarging dose dial 202 and the housing 201 is bigger than the thread connection 222/229 between the dose dial 232 and the nut 208 (fixed in the housing 201), the enlarging dose dial 202 will move a bigger axial distance than the dose dial 232 and more axial space for numbers along the axis of the device is provided. As the enlarging dose dial 202 at the same time rotates faster than the dose dial 232 more rotational space for numbers is provided as well. The track connection 251/252 between the dose dial 232 and the enlarging dose dial 202 can also be straight in which case the angular space for the numbers around the circumference of the enlarging dose dial 202 will be the same as for the dose dial 232.

Figure 14:
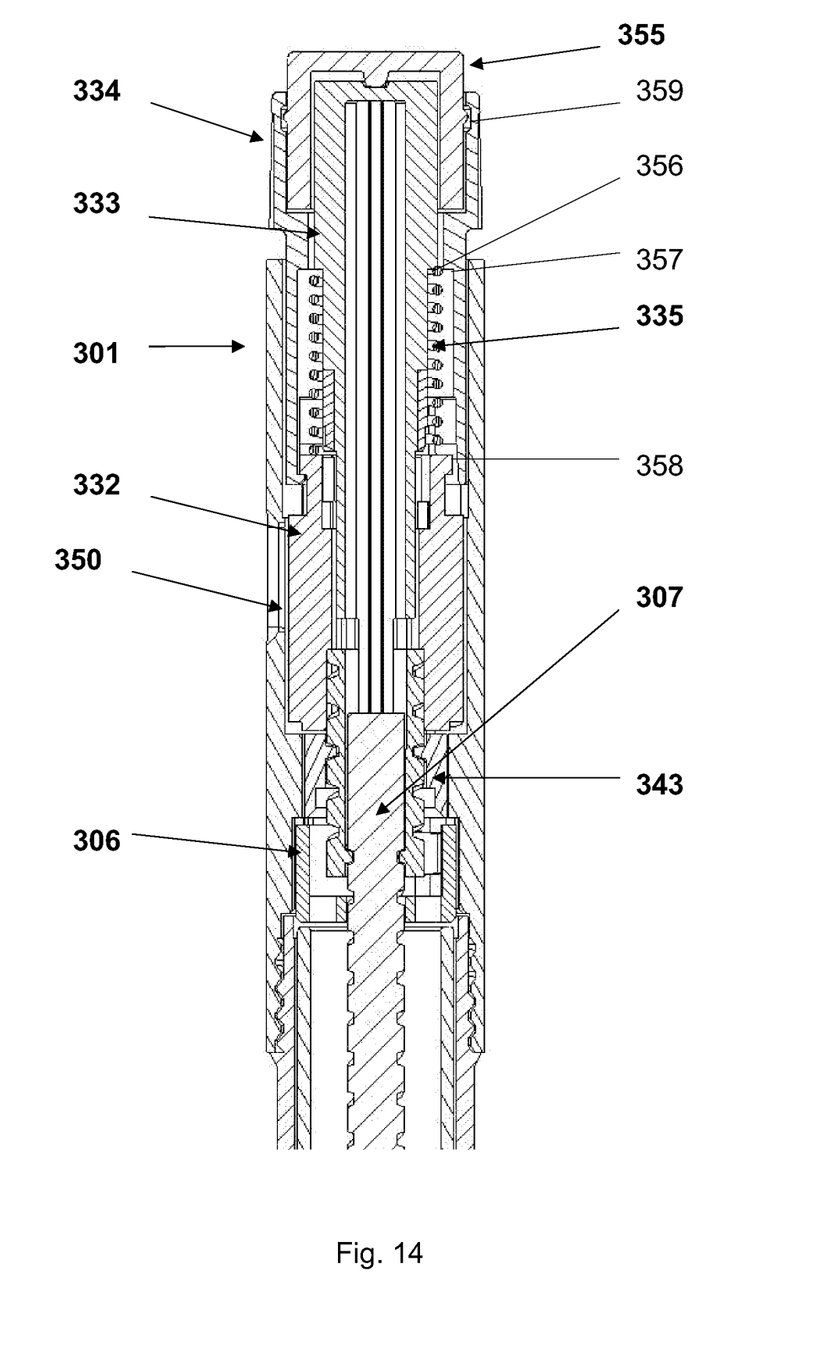

On FIG. 14 yet another embodiment of the device is shown. Parts and features not referred to corresponds to parts and features of the embodiment described in FIGS. 6-11. As it is only the resistance from the ratchet 306 and the cartridge that prevents the screw 307 from moving forward when a set dose is reset, it is important not to generate resistance that brings the connector 333 and thereby the screw 307 along in the rotational dose resetting direction. In the embodiment shown in FIGS. 6-11 the spring 135 applies a force to the connector 133 even when the dose selector 134 is not pushed down by a user, and consequently the spring force must be so low that the torque on the dose selector 134 arising from the spring force is lower than the torque arising from the ratchet 306 in the non-locking direction. This can be difficult to achieve as the spring force must be high enough to ensure that the dose selector 134 always re-engages the driver 150 (comprising the dose dial 132 and the threaded part 143 fixed together) after an injection has been fulfilled. In the embodiment shown in FIG. 14 another spring configuration is suggested, where the spring force is relieved from the connector 333 to the dose selector 334 when the dose selector 334 and the dose driver 350 have re-engaged. To make this feasible it is not possible to transmit the push force from the dose selector 334 to the driver 350 and a push-button 355 has therefore been introduced in an opening in the dose selector 334 protruding out of the housing 301. When the device is ready to set a dose the spring 335 is in one end applying a force to the end surface 358 of the dose dial 332 and in the other end to the recess 356 on the dose selector 334, and as the dose selector 334 and the dose dial 332, and thereby the driver 350, rotate together during dose setting, the spring force does not affect any other parts. When a dose has been set and the push-button 355 is pushed down to inject the set dose the connector 333 moves axially relative to the dose selector 334 and the recess 357 will pass the recess 356 and act on the spring 335. During injection the connector 333 and the driver 350 are rotationally coupled together, and the spring 335, the connector 333 and the driver 350 all rotate together. When the user has completed the injection and relieves the pressure on the push-button 355, the connector 333 and the push-button 355 move up until the recess 356 passes the recess 357 and the spring force is transmitted to the recess 357 on the dose selector 334. The push-button 355 has a ring-formed snap feature 359, which allows the push-button 355 to move a distance relative to the dose selector 334. This is to make it possible for the recesses 356, 357 to pass each other and at the same time to prevent the push-button 355 and the connector 333 from disengaging from the device.

The invention claimed is:

1. An injection device comprising:
a housing containing a first thread,
a screw having a second thread and a non-circular cross section, and
a driver having a third thread and a fourth thread,
wherein:
the screw rotates during injection,
the third thread of the driver engages the first thread in the housing, and the fourth thread of the driver engages the second thread of the screw,
the third thread and the fourth thread of the driver have the same leads and are headed in a same direction,
during dose setting, the driver rotates and moves axially while the screw does not rotate or move axially, and
during injection, the driver rotates together with the screw.

2. An injection device according to claim 1, wherein:
an enlarging dose dial is engaged with the housing by a fifth thread having a higher lead than the threads on the driver, and
the driver is engaged with the enlarging dose dial via a track allowing axial movement between the driver and the enlarging dose dial.

3. An injection device according to claim 1 wherein:
during injection, the screw and the driver are rotationally coupled by means of a connecting tube that is engaged with the non-circular cross section of the screw, and the connecting tube, during injection, is rotationally coupled to the driver.

4. An injection device according to claim 3, wherein:
a bi-directional ratchet is provided between a dose dial and the connecting tube, and
the bi-directional ratchet, during dose setting, indexes the dose dial on specific rotational positions around a revolution.

5. An injection device according to claim 1, wherein:
the driver is coupled to a dose selector during dose setting and decoupled during injection, and
the driver and the dose selector move a same distance during dose setting and injection.

6. An injection device according to claim 1, wherein:
a uni-directional ratchet is rotationally coupled to the screw and axially movable relative to the screw but not relative to the housing, and
the ratchet prevents the screw from moving back into the device towards a push-button end during dose setting and dose resetting.

* * * * *